US012708719B2

(12) United States Patent
Ryckalts

(10) Patent No.: US 12,708,719 B2
(45) Date of Patent: Aug. 18, 2026

(54) SYRINGE WITH AN IMPROVED NEEDLE RETRACTION MECHANISM

(71) Applicant: Roncadelle Operations SRL, Castel Mella (IT)

(72) Inventor: Erik Ryckalts, Castel Mella (IT)

(73) Assignee: Roncadelle Operations SRL, Castel Mella (IT)

(*) Notice: Subject to any disclaimer, the term of this patent is extended or adjusted under 35 U.S.C. 154(b) by 736 days.

(21) Appl. No.: 18/021,389

(22) PCT Filed: Aug. 19, 2021

(86) PCT No.: PCT/EP2021/073055
§ 371 (c)(1),
(2) Date: Feb. 14, 2023

(87) PCT Pub. No.: WO2022/038229
PCT Pub. Date: Feb. 24, 2022

(65) Prior Publication Data

US 2023/0293825 A1 Sep. 21, 2023

(30) Foreign Application Priority Data

Aug. 20, 2020 (EP) .................................... 20192013
Oct. 28, 2020 (EP) .................................... 20204245

(51) Int. Cl.
*A61M 5/32* (2006.01)
*A61M 5/315* (2006.01)

(52) U.S. Cl.
CPC ...... *A61M 5/3234* (2013.01); *A61M 5/31515* (2013.01); *A61M 2005/31521* (2013.01); *A61M 2005/323* (2013.01)

(58) Field of Classification Search
CPC ................ A61M 5/3234; A61M 5/322; A61M 2005/323; A61M 2005/3241
See application file for complete search history.

(56) References Cited

U.S. PATENT DOCUMENTS 5,190,526 A * 3/1993 Murray ............... A61M 5/3234 604/110
5,211,628 A * 5/1993 Marshall ............. A61M 5/3234 604/110

(Continued)

FOREIGN PATENT DOCUMENTS

EP 0505330 A1 9/1992
EP 2229968 A1 9/2010

(Continued)

OTHER PUBLICATIONS

WIPO, ISR for PCT/EP2021/073055, Nov. 22, 2021.

*Primary Examiner* — Laura A Bouchelle
(74) *Attorney, Agent, or Firm* — Hodgson Russ LLP

(57) ABSTRACT

The present invention relates to a syringe with an improved needle retraction mechanism, comprising: (a) a cylindrical barrel, (b) a needle holder, (c) a hollow plunger, (d) a rod, (e) an extractor element, and (f) a recovery tension or compression spring, the extractor element being movably displaceable from an advanced position to a retracted position, said extractor element having a male protrusion to engage the internal cavity of the needle holder to join the extractor element to the needle holder, and hooking means defining a connection between the plunger and the extractor element, and wherein the axial hole of the plunger is defined by a plurality of bendable flanges which are configured to slide over the needle holder, said bendable flanges thereby bending outwardly and expanding the axial hole of the plunger, and whereby the extractor element is disconnected from said plunger and is retracted towards its retracted position. The present invention also relates to a syringe kit wherein the syringe is provided with an improved needle retraction mechanism as described herein.

27 Claims, 7 Drawing Sheets

(56) References Cited

U.S. PATENT DOCUMENTS

| | | | | | |
|---|---|---|---|---|---|
| 5,378,240 | A * | 1/1995 | Curie | A61M 5/3234 |
| | | | | 604/110 |
| 5,531,694 | A * | 7/1996 | Clemens | A61M 5/3232 |
| | | | | 604/110 |
| 6,632,199 | B1 * | 10/2003 | Tucker | A61M 5/3134 |
| | | | | 604/192 |
| 7,351,224 | B1 | 4/2008 | Shaw | |
| 7,393,340 | B2 * | 7/2008 | Maggioni | A61M 5/3234 |
| | | | | 604/110 |
| 9,480,799 | B2 * | 11/2016 | Schraga | A61M 5/3234 |

FOREIGN PATENT DOCUMENTS

| | | | |
|---|---|---|---|
| EP | 2371407 | A1 | 10/2011 |
| JP | H0584300 | A | 4/1993 |
| JP | H05503437 | A | 6/1993 |
| JP | H06508770 | A | 10/1994 |
| JP | 3114203 | B2 | 9/2000 |
| JP | 2002085563 | A | 3/2002 |
| JP | 2003164524 | A | 6/2003 |
| JP | 2013510596 | A | 3/2013 |
| WO | 9103269 | A1 | 3/1991 |
| WO | 9107198 | A1 | 5/1991 |

* cited by examiner 2
17
6
11
12
13
4
3
9
8
14
10
5

2
16
6
17
11
12
13
4
3
9
8
14
10
5

SYRINGE WITH AN IMPROVED NEEDLE RETRACTION MECHANISM

FIELD OF THE INVENTION

The present invention relates to a safety syringe with a retractable needle.

More in particular, the invention relates to a syringe with an improved needle retraction mechanism.

BACKGROUND

Medical syringes are well-known in the art and comprise a large variety of designs, each with their specific advantages and applications. A specific type of syringe relates to the so-called safety syringe, which serves to protect healthcare workers and other individuals from accidental needlestick injuries and to prevent re-use of the syringe. The dangers originating from the reutilization of already used syringes and the problems caused by the abandonment thereof in public places are well-known. Over recent years, the importance of the safety syringe has increased, as many governments and safety bodies started focusing on the issues of needlestick injuries and re-use prevention.

A general problem however associated with present safety syringes is their relative complexity and/or unclear operation. A healthcare worker operating a safety syringe is often unsure as to how to engage the mechanisms which retracts the needle and/or which locks the needle safely inside the syringe. Furthermore, even if the mechanism has been engaged, a healthcare worker is in doubt about whether or not the needle has been retracted correctly and/or if said retraction has been fully completed. Additionally, present retraction mechanisms render the syringe design needlessly complex and inherently lead to some other disadvantages, e.g. a mediocre liquid- and/or air-tightness, and inaccurate liquid dosing. These disadvantages create additional uncertainties for the healthcare worker as he or she can no longer be sure about the exact volume injected.

A safety syringe with a retracting needle is exemplified in EP 0 505 330. Although the syringe comprises a working needle retraction mechanism, a healthcare worker would need to be provided with detailed instructions on how to operate the syringe correctly. Whereas operating a normal syringe simply comprises the pushing of a plunger rod until the syringe has emptied, the syringe design according to EP '330 needs to be handled diligently. In a first pushing stroke the syringe is emptied. In order to engage the retraction mechanism, the operator however needs to push the plunger rod explicitly further during a second pushing stroke. The need for said second push is not only contra-intuitive, it is furthermore highly unclear when needle retraction is engaged, and whether or not it is fully completed. To add thereto, the retraction mechanism according to EP '330 is a two-stage retraction: firstly the needle holder is coupled to the extractor element, it is only in a second stage that the retraction mechanism is engaged and actually retracts the needle. It is therefore possible for an operator to willingly or unwillingly only engage the mechanism in part.

Another safety syringe is disclosed by U.S. Pat. No. 5,190,526. The retraction mechanism is quite complex as the wall of the syringe barrel is shaped in order to fit a plurality of spherical bearings. The unusual shape of the syringe barrel unavoidably reduces liquid- and/or air-tightness of the sealing between the plunger and the barrel, and vastly reduces the volumetric accuracy of liquid dosing. A healthcare worker operating the syringe according to U.S. Pat. No. '526 will thus be unsure about the exact volume injected. As the retraction mechanism of U.S. Pat. No. '526 comprises a two-stage retraction, the operator will furthermore be unsure about whether or not the retraction mechanism has been engaged correctly. Also WO 91/03269 and EP 2 229 968 describe syringes with safety retraction mechanisms. JP H05 503437 describes a pre-filled syringe.

The present invention aims to resolve at least some of the problems and disadvantages mentioned above.

SUMMARY OF THE INVENTION

The present invention and embodiments thereof serve to provide a solution to one or more of above-mentioned disadvantages. To this end, the present invention relates to a syringe with an improved needle retraction mechanism according to claim 1, having the advantage that the syringe is intuitively operable for a healthcare worker, or any other individual.

The invention can be operated like a regular syringe, wherein the retraction mechanism is automatically engaged as soon as the syringe has been emptied. By the provision of bendable flanges on the plunger, the retraction mechanism is allowed to be engaged in one fluid motion which does not differ from normal operation of a regular syringe. Consequently, the syringe according to the present invention does not leave the operator in doubt about whether or not retraction has been correctly and/or completely engaged, nor does the operator have the possibility to re-use the syringe. Furthermore, as no volumetric adaptations to the barrel are needed, the volumetric accuracy of injection is optimally preserved.

Preferred embodiments of the device are shown in any of the claims 2 to 14.

The present invention also relates to a syringe kit, preferably a pre-filled syringe kit with a needle retraction mechanism according to claim 15, having the advantage that the syringe kit is ready to use, safe to use, and intuitively operable for a healthcare worker, or any other individual.

The invention can be operated like a regular syringe, with the advantage that the retraction mechanism is automatically engaged as soon as the syringe has been emptied. By the provision of bendable flanges on the plunger, the retraction mechanism is allowed to be engaged in one fluid motion which does not differ from normal operation of a regular syringe. Consequently, the syringe kit according to the present invention does not leave the operator in doubt about whether or not retraction has been correctly and/or completely engaged, nor does the operator have the possibility to re-use the syringe. Furthermore, as no volumetric adaptations to the barrel are needed, the volumetric accuracy of injection is optimally preserved. The syringe kit being comprised of two parts, i.e. the syringe assembly and the injection assembly, has the additional advantage that the syringe kit can be in both an assembled and disassembled kit configuration.

In some embodiments of the invention, the syringe is a pre-filled syringe.

Preferred embodiments of the syringe kit are shown in any of the dependent claims.

The invention also relates to the use of the syringe kit according to claim 27.

In a final aspect, the invention concerns a method of manufacturing a syringe kit according to claim 26.

FIGURES

FIG. 1A shows an overall view of a syringe according to an embodiment of the present invention in its advanced position before engagement of the needle retraction mechanism.

FIG. 1B shows an overall view of a syringe according to an embodiment of the present invention in its retracted position after engagement of the needle retraction mechanism.

FIG. 2A shows a detailed view of a needle retraction mechanism of a syringe according to an embodiment of the present invention before engagement of the mechanism.

FIG. 2B shows a detailed view of a needle retraction mechanism of a syringe according to an embodiment of the present invention during engagement of the mechanism.

FIG. 2C shows a detailed view of a needle retraction mechanism of a syringe according to an embodiment of the present invention during advanced engagement of the mechanism.

FIG. 3 shows a detailed view of a needle retraction mechanism of a syringe according to an embodiment of the present invention comprising a sealing ring fitted between the extractor element and the hollow plunger.

FIG. 4 shows a detailed view of a needle retraction mechanism of a syringe according to an embodiment of the present invention comprising a sealing ring fitted between the extractor element and the hollow plunger, and a fitting for an interchangeable needle holder.

FIG. 5 shows an overall view of a syringe kit according to an embodiment of the present invention in its advanced position before engagement of the needle retraction mechanism.

FIG. 6 shows an overall view of a syringe kit according to an embodiment of the present invention in its retracted position after engagement of the needle retraction mechanism.

FIG. 7 shows an embodiment of the invention wherein the hollow nose end of the needle holder is further equipped with an internal annular ring.

FIG. 8 shows an embodiment of the invention wherein the extractor element is further equipped with a dead space filler and the inner surface of the plunger is equipped with an annular ring.

FIG. 9 shows a plunger cap and retraction element equipped with a plurality of spring retention fins, which fins are shown retaining the proximal and distal end of the recovery tension spring onto the plunger cap and the extractor element respectively.

FIG. 10 shows a gasket between the outer surface of the needle holder and the internal surface of the hollow nose of the barrel.

DETAILED DESCRIPTION OF THE INVENTION

The present invention concerns a syringe with an improved needle retraction mechanism.

Unless otherwise defined, all terms used in disclosing the invention, including technical and scientific terms, have the meaning as commonly understood by one of ordinary skill in the art to which this invention belongs. By means of further guidance, term definitions are included to better appreciate the teaching of the present invention.

As used herein, the following terms have the following meanings:

"A", "an", and "the" as used herein refers to both singular and plural referents unless the context clearly dictates otherwise. By way of example, "a compartment" refers to one or more than one compartment.

"Comprise", "comprising", and "comprises" and "comprised of" as used herein are synonymous with "include", "including", "includes" or "contain", "containing", "contains" and are inclusive or open-ended terms that specifies the presence of what follows e.g. component and do not exclude or preclude the presence of additional, non-recited components, features, element, members, steps, known in the art or disclosed therein.

Furthermore, the terms first, second, third and the like in the description and in the claims, are used for distinguishing between similar elements and not necessarily for describing a sequential or chronological order, unless specified. It is to be understood that the terms so used are interchangeable under appropriate circumstances and that the embodiments of the invention described herein are capable of operation in other sequences than described or illustrated herein.

The recitation of numerical ranges by endpoints includes all numbers and fractions subsumed within that range, as well as the recited endpoints.

Whereas the terms "one or more" or "at least one", such as one or more or at least one member(s) of a group of members, is clear per se, by means of further exemplification, the term encompasses inter alia a reference to any one of said members, or to any two or more of said members, such as, e.g., any ≥3, ≥4, ≥5, ≥6 or ≥7 etc. of said members, and up to all said members.

A first aspect of the present invention relates to a syringe with an improved needle retraction mechanism, comprising:

a. a cylindrical barrel comprising a hollow body and a hollow nose end;
b. a needle holder positioned in said nose end, wherein said needle holder comprises an internal cavity;
c. a hollow plunger positioned within said hollow body of said cylindrical barrel;
d. a rod connected to or integral with said plunger and extending into said hollow body of said cylindrical barrel, wherein each of said rod and said plunger has an axial hole passing therethrough;
e. an extractor element is positioned within said axial hole of said plunger and within said hole of said rod;
f. a recovery tension or compression spring connected to said extractor element;

said extractor element being movably displaceable from an advanced position, surrounded by said plunger with a portion protruding past the distal end of or from said plunger in the needle holder direction, and a retracted position, fully retracted into said rod, positioned away from said needle holder; said extractor element having a male protrusion, protruding past the distal end of or from said plunger in said advanced position to engage said internal cavity of said needle holder to join said extractor element to said needle holder, and hooking means defining a connection between said plunger and said extractor element to maintain said extractor element in said advanced position and to maintain the recovery spring under tension or compression; and wherein the axial hole of the plunger is defined by a plurality of bendable flanges which are configured to slide over the needle holder, said bendable flanges thereby bending outwardly and expanding the axial hole of the plunger, and whereby the extractor element is disconnected from said plunger and is retracted towards its retracted position.

In the context of the present invention, the term "syringe" relates to a simple reciprocating pump consisting of a "plunger" or "piston" that fits tightly within a cylindrical tube, called a "barrel". The plunger can be linearly pulled and pushed along the inside of the barrel, allowing the syringe to take in and expel liquid through a discharge orifice located at the nose end of the barrel. According to the invention, the nose end is fitted with a needle holder, which needle holder comprises a needle, e.g. a hypodermic needle. Syringes as described herein are frequently used in clinical medicine to administer injections, or to infuse intravenous therapy into the bloodstream.

The term "needle retraction mechanism" indicates any mechanism which allows the automatic retraction of the needle holder including the needle inside the syringe, in order to prevent re-use of the syringe and/or to lower the risk of needle-stick injury.

The terms "plunger" and "rod", especially the wording "plunger connected to said rod", need to be interpreted as both single- and multiple-piece elements, which are both known in the art. In particular, the plunger and the rod can be provided as a single piece, whereas they can also comprise independent pieces connected to each other via commonly used connecting means.

The wording "extractor element" relates to the specific element of the retraction mechanism which extracts the needle and pulls it inside the syringe. According to the present invention, actual retraction is achieved by means of a "recovery tension or compression spring", indicating that the spring is under tension or compression during operation of the syringe, and compresses or expands to its resting state upon engagement of the retraction mechanism, thereby retracting the extractor element and the needle holder coupled thereto. In this context, the position before retraction is referred to as the "advanced position", while the position after retraction is referred to as the "retracted position".

The terminology "hooking means" relates to any means which reversable interconnect two or more elements to each other. Specific hooking means comprise complementary protrusions and/or indentations, areas of higher friction or adhesion etc.

The wording "bendable flanges" herein relates to any bendable parts extending from the plunger in the direction of the needle holder, wherein their bendable nature is the result of e.g. provision of a deformable material, provision of a certain thinness to the flanges etc.

The syringe according to the present invention comprises a vastly improved needle retraction mechanism, having the advantage that the syringe is intuitively operable for a healthcare worker, or any other individual. The invention can be operated like a regular syringe, wherein the retraction mechanism is automatically engaged as soon as the syringe has been emptied. Self-locking syringes known in the art commonly require the operator to perform multiple and/or additional steps in order to engage the mechanism, i.e. the plunger has to be pushed further forward although the syringe has already been emptied, the coupling of the needle holder to the extractor element and the decoupling of the extractor element from the plunger taking place in separate movements etc. The present invention comprising bendable flanges on the plunger however allows the retraction mechanism to be engaged in one fluid motion which does not differ from normal operation of a regular syringe. The substantially conical shape of the distal end of the male protrusion of the extractor element constitute a steep angle over which the bendable grips of the needle holder can slide which requires said bendable grips to bend only a small amount in order to engage said male protrusion. Furthermore, the entrance to the needle holder cavity as formed by the bendable grips of the said needle holder are characterized by a conical depression complementary to the distal end of the male protrusion. In this way, the perceivable resistance felt by the user is advantageously kept to a minimum. The outer perimeter of the bendable grips of the needle holder are also provided with a substantially angled surface which permits, advantageously, to further reduce the resistance felt by the user as the bendable flanges of the of the hollow plunger ride over said angled outer surface of the needle holder. The only tactile feedback provided to the user during operation of the syringe are the plunger reaching the end of the barrel and the impact of the extractor element against the retraction spring upon retraction of the needle. Consequently, the syringe according to the present invention does not leave the operator in doubt about whether or not retraction has been correctly and/or completely engaged, nor does the operator have the possibility to re-use the syringe. As a result, any risk of needle-stick injuries has been eliminated and re-use has been effectively prevented. Furthermore, as no volumetric adaptations to the barrel are needed, the volumetric accuracy of injection is optimally preserved.

By preference, said plurality of bendable flanges are bendable over an angle of between 0° and −45° relative to the axial centerline of the syringe. By allowing the bendable flanges to bend over the aforementioned angles, the extractor element can be decoupled from the plunger in one fluid motion. The bendable flanges being bent over an angle of e.g. −40° relative to the axial centerline of the syringe ensure the locking of the extractor element inside the hollow plunger, wherein the recovery tension or compression spring is maintained under tension or compression. As soon as the needle holder has substantially entered the axial cavity of the plunger, thereby opening the bendable flanges up to an angle of e.g. −5° relative to the axial centerline of the syringe, the extractor element is released from the plunger. It follows that the recovery tension or compression spring respectively compresses or expands, and respectively pulls or pushes the extractor element coupled to the needle holder inside the hollow plunger, thereby safely locking away the needle inside the syringe.

More by preference, said plurality of bendable flanges are bendable over an angle of between 0° and −40° relative to the axial centerline of the syringe, even more by preference of between 0° and −35°, between 5° and −35°, between 5° and 30°, or between 10° and 30° relative to the axial centerline of the syringe.

According to a further or another embodiment, said plurality of bendable flanges comprises at least two bendable flanges. The presence of two bendable flanges allows the extraction element to be kept in place inside the hollow plunger. Upon entering the needle holder in between the bendable flanges, the axial hole of the plunger is expanded evenly and symmetrically, thereby allowing the straight retraction of the extractor element and the needle holder coupled thereto inside the syringe. Due to the configuration described herein, the needle retraction mechanism can be engaged by the operator, wherein only slight resistance is noticeable. Therefore, operating the syringe according to the present invention does not feel markedly different to the operator compared to operating a regular syringe. As a result, operating the syringe according to the invention is particularly intuitive to a healthcare worker or any other individual.

By preference, said plurality of bendable flanges comprises at least three bendable flanges, more by preference at least four bendable flanges, at least five or at least six bendable flanges.

In some embodiments, the hooking means are complementary protrusions extending from both the hollow plunger and the extractor element. Such protrusions allow a smooth decoupling of the extractor element from the hollow plunger by outwardly expanding the bendable flanges.

According to a further or another embodiment, said internal cavity of the needle holder is defined by a plurality of bendable grips, which are configured to slide over the male protrusion of the extractor element, said bendable grips thereby bending outwardly, and whereby the male protrusion of the extractor element is inserted inside the internal cavity of the needle holder. Connection of the extractor element to the needle holder is particularly smooth, for which operation of the syringe according to the present invention does not feel markedly different to the operator compared to operating a regular syringe. Meanwhile, the provided bendable grips allow a sturdy and irreversible coupling of the extraction element to the needle holder. The needle retraction mechanism thus ensures effective retraction of the needle holder including the needle inside the syringe.

By preference, the plurality of bendable grips are configured to slide inside the axial hole of the plunger, said bendable grips thereby bending inwardly, and whereby the male protrusion of the extractor element is locked inside the internal cavity of the needle holder. Upon engagement of the retraction mechanism, the described bending of the bendable grips towards the inside of the syringe furthermore ensures a sturdy coupling of the extractor element to the needle holder including the needle. Said coupling is particularly effective once retraction has started and prevents that the male protrusion should be inadvertently decoupled from the internal cavity of the needle holder.

According to a further or another embodiment, said plurality of bendable grips are bendable over an angle of between −20° and 20° relative to the axial centerline of the syringe. The bendable grips being bent over an angle of e.g. 15° relative to the axial centerline of the syringe ensure the smooth insertion of the male protrusion of the extraction element inside the internal cavity of the needle holder. As soon as the needle holder has substantially entered the axial cavity of the plunger, thereby opening the bendable flanges, the flanges are pushing back the bendable grips, bending to an angle of e.g. −15° relative to the axial centerline of the syringe. This ensures the male protrusion being irreversibly coupled, thereby preventing that the male protrusion should be inadvertently decoupled from the internal cavity of the needle holder.

By preference, said plurality of bendable grips are bendable over an angle of between −15° and 15° relative to the axial centerline of the syringe, more by preference of between −10° and 10°, between −5° and 10°, or between −5° and 5° relative to the axial centerline of the syringe.

In some embodiments, said plurality of bendable grips comprises at least two bendable grips. The presence of two bendable grips allows the inside cavity of the needle holder to be expanded evenly and symmetrically, thereby allowing the straight entrance of the male protrusion inside the internal cavity of the needle holder. Furthermore, upon further retraction the internal cavity of the needle holder is evenly and symmetrically narrowed down around the male protrusion, thereby allowing safe coupling of the extractor element to the needle holder. Due to the configuration described herein, the needle retraction mechanism can be engaged by the operator, wherein only slight resistance is noticeable. Therefore, operating the syringe according to the present invention does not feel markedly different to the operator compared to operating a regular syringe. As a result, operating the syringe according to the invention is particularly intuitive to a healthcare worker or any other individual.

By preference, said plurality of bendable grips comprises at least three bendable grips, more by preference at least four bendable grips, at least five bendable grips or at least six bendable grips.

According to some embodiments, the needle holder is air-tightly configured inside the hollow nose end, wherein the inside wall of the hollow nose end and the outside wall of the needle holder are complementary, conically shaped.

The syringe according to the present invention, according to some embodiments comprises a gasket, which gasket is fitted surrounding the plunger at its needle holder end, and wherein said gasket is fitted between the outside of the plunger and the inside of the hollow body of the cylindrical barrel, and wherein the gasket at least partially overlaps the plurality of bendable flanges.

In the light of the present invention, the term "gasket" relates to a mechanical seal which fills the space between two or more mating surfaces, generally to prevent leakage from or into the joined objects while under compression. In the present case, the gasket is fitted between the outside of the plunger and the inside of the hollow body of the cylindrical barrel.

While the gasket preliminary serves the purpose of making the syringe liquid- and air-tight, the gasket additionally provides for an adequate resistance counteracting the expansion of the bendable flanges and/or the expansion of the bendable grips. As a result, the single-stage coupling of the extraction element to the needle holder and the retraction of said two elements inside the hollow plunger is further improved as the gasket allows just the right amount of expansion of the bendable flanges over the needle holder and/or just the right amount of compression of the bendable grips over the male protrusion of the extraction element.

In some embodiments, the hollow body and the hollow nose end of the cylindrical barrel are provided as a single unit. These embodiments only allow the syringe to be fitted with a single type of needle holder and/or needle. Among others, such syringes comprise prefilled syringes, disposable syringes etc. Said embodiments are particularly advantageous as the needle holder cannot be removed from the syringe at all without actually breaking the syringe.

In some embodiments, the hollow body and the hollow nose end of the cylindrical barrel are provided as two independent units, wherein the hollow body extends in a cylindrical or conical fitting comprising an axial hole, which axial hole of the fitting is accommodated to at least partly receive the hollow nose end, and which fitting is furthermore configured with connecting means for connecting the hollow nose end to the hollow body of the cylindrical barrel. Before use of the syringe, said embodiments allow the selection of a certain needle holder, in particular a certain needle, to be fitted in the hollow nose end of the syringe. By coupling the hollow nose end to the hollow body of the cylindrical barrel, the needle holder cannot be removed from the syringe once coupled, meanwhile leaving the operator a choice of needle before injection.

According to a further or another embodiment, the extractor element is air-tightly configured inside the hollow plunger by means of a sealing ring fitted in between the inside wall of the plunger and the outside wall of the extractor element. The sealing ring fitted between the plunger and the extractor element thus ensures that no pressure is lost as long as the extractor element is coupled onto the plunger. As soon as the syringe has been completely emptied and the retraction mechanism is engaged, the sealing ring is no longer fitted in between, and accordingly pressure is lost.

In some embodiments, the recovery spring is a recovery tension spring, which is positioned within the hole of the rod, and is connected to the extractor element. In these embodiments, the recovery tension spring preferably extends along the length of the rod. Alternatively, in some embodiments, the recovery spring is a recovery compression spring. Such recovery compression spring could be fitted between the extractor element and the hollow plunger on the side of the needle holder.

According to some embodiments, the bendable flanges consist of a material which has an elastic modulus of between 600 and 2000 N/mm$^2$, more preferably between 600 and 2500 N/mm$^2$. Within said range, a desirable amount of bending is achieved, allowing smooth operation of the improved retraction mechanism according to the present invention. In this context, the term “elastic modulus” needs to be interpreted as a measure for an object or substance’s resistance to being deformed elastically, i.e. non-permanently) when a stress is applied to it. The elastic modulus of an object is defined as the slope of its stress-strain curve in the elastic deformation region.

The bendable flanges according to some embodiments of the present invention, consist of a material which has an ultimate tensile strength, or tensile strength at break, of at least 15 N/mm$^2$, more preferably at least 20 N/mm$^2$. As such, the bendable flanges are able to withstand the various stresses invoked on the flanges by the retraction mechanism without breaking through. The wording “ultimate tensile strength” or “tensile strength at break” is to be interpreted as the maximal stress that a material can withstand while being stretched or pulled before breaking. The ultimate tensile strength is usually determined by performing a tensile test and recording a stress-strain curve.

By preference, the bendable flanges consist of a material which has an elastic modulus of between 600 and 2000, more preferably between 600 and 2500 N/mm$^2$ and has an ultimate tensile strength of at least 15 N/mm$^2$, more preferably at least 20 N/mm$^2$. Consequently, an optimal balance is found between the amount of bending and the ultimate tensile strength or the bendable flanges, for which a smooth release of the extractor element from the hollow plunger is achieved.

According to some embodiments, the bendable grips consist of a material which has an elastic modulus of between 600 and 2000 N/mm$^2$, more preferably between 600 and 2500 N/mm$^2$. Within said range, a desirable amount of bending of the bendable grips of the needle holder is achieved, allowing smooth operation of the improved retraction mechanism according to the present invention.

The bendable grips according to some embodiments of the present invention, consist of a material which has a ultimate tensile strength, or tensile strength at break, of at least 15 N/mm$^2$, more preferably at least 20 N/mm$^2$. As such, the bendable grips are able to withstand the various stresses invoked on the grips by the retraction mechanism without breaking through.

By preference, the bendable grips consist of a material which has an elastic modulus of between 600 and 2000 N/mm$^2$, more preferably between 600 and 2500 N/mm$^2$ and has an ultimate tensile strength of at least 15 N/mm$^2$, more preferably at least 20 N/mm$^2$. Consequently, an optimal balance is found between the amount of bending and the ultimate tensile strength or the bendable grips, for which a smooth coupling of the male protrusion of the extractor element to the needle holder is achieved.

In some embodiments, the extractor element is air-tightly configured inside the hollow plunger, wherein the inside wall of the hollow plunger and the outside wall of the extractor element are complementary, conically shaped.

In some embodiments of the invention, the syringe is a pre-filled syringe.

In a further aspect, the present invention relates to a syringe kit, preferably a pre-filled syringe kit, said syringe kit comprising a syringe assembly and an injection assembly, said syringe assembly comprising:

a. a cylindrical barrel comprising a hollow body, wherein the hollow body is at least partly filled with an injectable liquid;
b. a hollow plunger positioned within said hollow body of said cylindrical barrel;
c. a rod connected to or integral with said plunger and extending into said hollow body of said cylindrical barrel, wherein each of said rod and said plunger has an axial hole passing therethrough;
d. an extractor element is positioned within said axial hole of said plunger and within said hole of said rod;
e. a recovery tension or compression spring connected to said extractor element; and said injection assembly comprising:

a. a hollow nose end; and
b. a needle holder positioned in said nose end, wherein said needle holder comprises an internal cavity; wherein the syringe assembly and the injection assembly respectively comprise a first connective part and a second connective part, said first and second connective part are configured to allow both a closed kit configuration and an open kit configuration, said closed kit configuration comprising the air-tight connection of the syringe assembly to the injection assembly, wherein the internal cavity of the needle holder and the hollow body of the cylindrical barrel are configured to form a continuous channel which allows the passage of the injectable liquid, and said open kit configuration comprising the air-tight sealing of the syringe assembly without connection of the injection assembly;

the extractor element is movably displaceable from an advanced position, surrounded by said plunger with a portion protruding past the distal end of or from said plunger in the first connective part direction, and a retracted position, fully retracted into said rod, positioned away from said first connective part;

the extractor element has a male protrusion, protruding past the distal end of or from said plunger in said advanced position to engage said internal cavity of said needle holder to join said extractor element to said needle holder, and hooking means defining a connection between said plunger and said extractor element to maintain said extractor element in said advanced position and to maintain the recovery spring under tension or compression;

wherein the axial hole of the plunger is defined by a plurality of bendable flanges which are configured to slide over the needle holder, said bendable flanges thereby bending outwardly and expanding the axial hole of the plunger, and whereby the extractor element is disconnected from said plunger and is retracted towards its retracted position.

In the context of the present invention, the terminology of "syringe assembly" and "injection assembly" relate to two distinct parts of the "syringe kit" as described herein. As the kit of the present invention can be both in an assembled and disassembled kit configuration, for easier reference, the syringe kit in its assembled configuration and/or its working state is referred to as "syringe".

The syringe kit according to the present invention comprises a vastly improved needle retraction mechanism, having the advantage that the syringe kit is ready to use, safe to use, and intuitively operable for a healthcare worker, or any other individual. The invention can be operated like a regular syringe, wherein the retraction mechanism is automatically engaged as soon as the syringe has been emptied.

In some embodiments, the first connective part and the second connective part of the respective syringe assembly and the injection assembly are air-tightly connected to each other. This particular embodiment refers to the assembled kit configuration and can be manufactured and/or supplied as such. In particular, a syringe manufacturer might manufacture the syringe assembly and the injection assembly, consequently fill the hollow body of the barrel with the injectable liquid, and air-tightly connect the syringe assembly to the injection assembly, thereby locking the injectable liquid inside the closed syringe kit. The syringe kit as described herein is particularly advantageous in case a certain injectable liquid is preferably used with a certain needle, and the syringe kit is immediately ready for use. In this respect, the kit is already provided with the adequate needle and does not leave the user in doubt about the choice of needle, nor about how the kit should be operated.

In some embodiments, the first connective part and the second connective part of the respective syringe assembly and the injection assembly are disconnected from each other, wherein the hollow body of the barrel is air-tightly sealed by means of a closure cap fitted to the first connective part of the syringe assembly. This particular embodiment refers to the disassembled kit configuration and can be manufactured and/or supplied as such. In particular, a syringe manufacturer might manufacture the syringe assembly and a multitude of injection assemblies, consequently fill the hollow body of the barrel with the injectable liquid, and air-tightly seal the hollow body of the barrel by means of the closure cap. The syringe kit as described herein is particularly advantageous in case a certain injectable liquid is to be used, but the choice of needle is not yet fixed. This leaves additional freedom of choice for both the manufacturer and the end user, as the choice of needle need not yet be decided on immediately. In particular, the syringe kit could be provided as a syringe assembly and a single injection assembly, wherein the user needs to remove the closure cap and connect both assemblies to each other before use. The choice of needle would then be delayed until the user purchases the needle kit with the manufacturer. Alternatively, the syringe kit could be provided as a syringe assembly and a plurality of different injection assemblies, wherein the user can choose the injection assembly right before use, i.e. by connecting the syringe assembly and the injection assembly of choice to each other.

An advantage of the syringe kit having a separate syringe assembly and injection assembly concerns the wide variety of packaging options, further improving ease of use for the user. While the syringe kit can be packaged as one, packaging can also be done of the syringe assembly and the injection assembly separately. In this regard, packaging multiple syringe assemblies and/or injection assemblies as so-called "nests" are considered a safe packaging method.

In an embodiment, the syringe kit as described herein provides for a syringe with needle retraction mechanism as described in one of the embodiments above and which are considered reprised here, in the context of the kit.

The present invention also relates to the use of the (pre-filled) syringe kit for the injection of the injectable liquid in a subject, wherein the syringe assembly and the injection assembly are connected to each other prior to injection.

A final aspect of the present invention relates to a method of manufacturing a syringe kit, preferably a pre-filled syringe kit, comprising:

assembling or providing a syringe assembly comprising the following parts:
- a. a cylindrical barrel comprising a hollow body;
- b. a hollow plunger positioned within said hollow body of said cylindrical barrel;
- c. a rod connected to or integral with said plunger and extending into said hollow body of said cylindrical barrel, wherein each of said rod and said plunger has an axial hole passing therethrough;
- d. an extractor element is positioned within said axial hole of said plunger and within said hole of said rod; and
- e. a recovery tension or compression spring connected to said extractor element assembling or providing a needle assembly comprising the following parts:
- a. a hollow nose end; and
- b. a needle holder positioned in said nose end, wherein said needle holder comprises an internal cavity; wherein the syringe assembly and the injection assembly respectively comprise a first connective part and a second connective part, said first connective part allowing the air-tight sealing of the hollow body of the barrel, and the air-tight connection to the second connective part of the injection assembly, wherein the internal cavity of the needle holder and the hollow body of the cylindrical barrel are configured to form a continuous channel which allows the passage of the injectable liquid, the extractor element is movably displaceable from an advanced position, surrounded by said plunger with a portion protruding past the distal end of or from said plunger in the first connective part direction, and a retracted position, fully retracted into said rod, positioned away from said first connective part; the extractor element has a male protrusion, protruding past the distal end of or from said plunger in said advanced position to engage said internal cavity of said needle holder to join said extractor element to said needle holder, and hooking means defining a connection between said plunger and said extractor element to maintain said extractor element in said advanced position and to maintain the recovery spring under tension or compression; and wherein the axial hole of the plunger is defined by a plurality of bendable flanges which are configured to slide over the needle holder, said bendable flanges thereby bending outwardly and expanding the axial hole of the plunger, and whereby the extractor element is disconnected from said plunger and is retracted towards its retracted position;

filling the hollow body of the cylindrical barrel at least partly with an injectable liquid; and air-tightly closing the hollow body of the cylindrical barrel.

By preference, the method manufactures the syringe kit according to one of the embodiments described above.

In a preferred embodiment of the invention, the syringe kit is a pre-filled syringe kit.

In particular, the filling and air-tightly closing steps can be performed by making use of a specific nested configuration of a plurality of syringe assemblies and/or injection assemblies. The so-called "nested" configuration is especially suitable to safely ship the sterile syringe assemblies from e.g. a syringe manufacturing site to a syringe filling site. The nested configuration comprises placement of a plurality of syringe assemblies in a packaging tray and sealing the tray with a sheet material, e.g. a Tyvek sheet. The packaging and its contents can thereafter be sterilized. Upon filling, the sheet material is removed and the syringe assemblies are entered into a filling line. The nested configuration as described herein can be either an upside-down configuration, or an downside-up configuration. So-called upside-down configuration provides filling of the syringe assemblies with the injectable liquid from the opening on the top of the barrel. Consequently, the syringe assembly can be either closed with a closure cap, or with the injection assembly. The so-called downside-up configuration allows the syringe assemblies to be filled from the lower part of the barrel and then closed by inserting the plunger therein.

DESCRIPTION OF FIGURES

The invention is further described by the following figures which illustrate the invention, and are not intended to, nor should they be interpreted to, limit the scope of the invention.

FIG. 1A and FIG. 1B respectively show the syringe in its advanced position and in its retracted position. The syringe shown herein has the advantage that the syringe is intuitively operable for a healthcare worker, or any other individual. The invention can be operated like a regular syringe, wherein the retraction mechanism is automatically engaged as soon as the syringe has been emptied. In particular, the bendable flanges 12 allow the retraction mechanism to be engaged in one fluid motion which does not differ from normal operation of a regular syringe. Furthermore, as no volumetric adaptations to the barrel 1 are needed, the volumetric accuracy of injection is optimally preserved. The bendable flanges 12 as depicted herein are particularly bendable over an angle of between 0° and −45° relative to the axial centerline of the syringe. The syringe shown herein comprises a gasket 14, which gasket is fitted surrounding the plunger 6 at its needle holder 4 end, and wherein said gasket 14 is fitted between the outside of the plunger 6 and the inside of the hollow body 2 of the cylindrical barrel 1, and wherein the gasket 14 at least partially overlaps the plurality of bendable flanges 12. In the depicted embodiment, the hollow body 2 and the hollow nose end 3 of the cylindrical barrel 1 are provided as a single unit. The extractor element 8 is air-tightly configured inside the hollow plunger 6 by means of a conical fitting 17 between the inside wall of the plunger 6 and the outside wall of the extractor element 8.

FIGS. 2A-2C show the barrel 1 comprising the hollow body 2, the hollow nose end 3, the needle holder 4, the internal cavity 5 of the needle holder 4, the hollow plunger 6, the rod 7, the extractor element 8, the recovery tension spring 9, the male protrusion 10 of the extractor element 8, the hooking means 11 between the plunger 6 and the extractor element 8, and the bendable flanges 12 of the hollow plunger 6. Furthermore, the internal cavity 5 of the needle holder 4 is defined by a plurality of bendable grips 13, which are configured to slide over the male protrusion 10 of the extractor element 8, said bendable grips 13 thereby bending outwardly, and whereby the male protrusion 10 of the extractor element 8 is inserted inside the internal cavity 5 of the needle holder 4. Connection of the extractor element 8 to the needle holder 4 is particularly smooth, for which operation of the syringe according to the present invention does not feel markedly different to the operator compared to operating a regular syringe. Meanwhile, the provided bendable grips 13 allow a sturdy and irreversible coupling of the extractor element 8 to the needle holder 4. The plurality of bendable grips 13 are furthermore configured to slide inside the axial hole of the plunger 6, said bendable grips 13 thereby bending inwardly, and whereby the male protrusion 10 of the extractor element 8 is locked inside the internal cavity 5 of the needle holder 4. Upon engagement of the retraction mechanism, the described bending of the bendable grips 13 towards the inside of the syringe furthermore ensures a sturdy coupling of the extractor element 8 to the needle holder 4 including the needle 21. The bendable grips 13 depicted herein are particularly bendable over an angle of between −20° and 20° relative to the axial centerline of the syringe. The syringe shown herein furthermore comprises a gasket 14, which gasket is fitted surrounding the plunger 6 at its needle holder 4 end, and wherein said gasket 14 is fitted between the outside of the plunger 6 and the inside of the hollow body 2 of the cylindrical barrel 1, and wherein the gasket 14 at least partially overlaps the plurality of bendable flanges 12. In the depicted embodiment, the hollow body 2 and the hollow nose end 3 of the cylindrical barrel 1 are provided as a single unit. The extractor element 8 is air-tightly configured inside the hollow plunger 6 by means of a conical fitting 17 between the inside wall of the plunger 6 and the outside wall of the extractor element 8. In particular, FIG. 2A shows the retraction mechanism right before engagement, FIG. 2B shows the male protrusion 10 sliding into the internal cavity 5 of the needle holder 4, thereby coupling the extractor element 8 to the needle holder 4. FIG. 2C shows further advancement of the retraction mechanism, as the bendable flanges 12 of the hollow plunger 6 are expanded, thereby releasing the extractor element 8 from the hollow plunger 6, meanwhile fastening the connection between the male protrusion 10 and needle holder 4 by bending the bending grips 13 inwardly.

FIG. 5 and FIG. 6 respectively show the syringe kit in its advanced position and in its retracted position. The syringe kit shown herein has the advantage that the syringe kit is intuitively operable for a healthcare worker, or any other individual, and is ready to use. The invention can be operated like a regular syringe, wherein the retraction mechanism is automatically engaged as soon as the syringe has been emptied. In particular, the bendable flanges 12 allow the retraction mechanism to be engaged in one fluid motion which does not differ from normal operation of a regular syringe. Furthermore, as no volumetric adaptations to the barrel 1 are needed, the volumetric accuracy of injection is optimally preserved. The bendable flanges 12 as depicted herein are particularly bendable over an angle of between 0° and −45° relative to the axial centerline of the syringe. The syringe kit shown herein comprises a gasket 14, which gasket is fitted surrounding the plunger 6 at its needle holder 4 end, and wherein said gasket 14 is fitted between the outside of the plunger 6 and the inside of the hollow body 2 of the cylindrical barrel 1, and wherein the gasket 14 at least partially overlaps the plurality of bendable flanges 12. The syringe assembly S and the injection assembly I respectively comprise a first connective part 19 and a second connective part 20, said first 19 and second connective part 20 are configured to allow both a closed kit configuration and an open kit configuration, said closed kit configuration comprising the air-tight connection of the syringe assembly S to the injection assembly I, wherein the internal cavity 5 of the needle holder 4 and the hollow body 2 of the cylindrical barrel 1 are configured to form a continuous channel which allows the passage of the injectable liquid L. It is furthermore shown that the injection assembly I comprises a needle 21 and a needle cap 18.

Figures 1A, 1B:
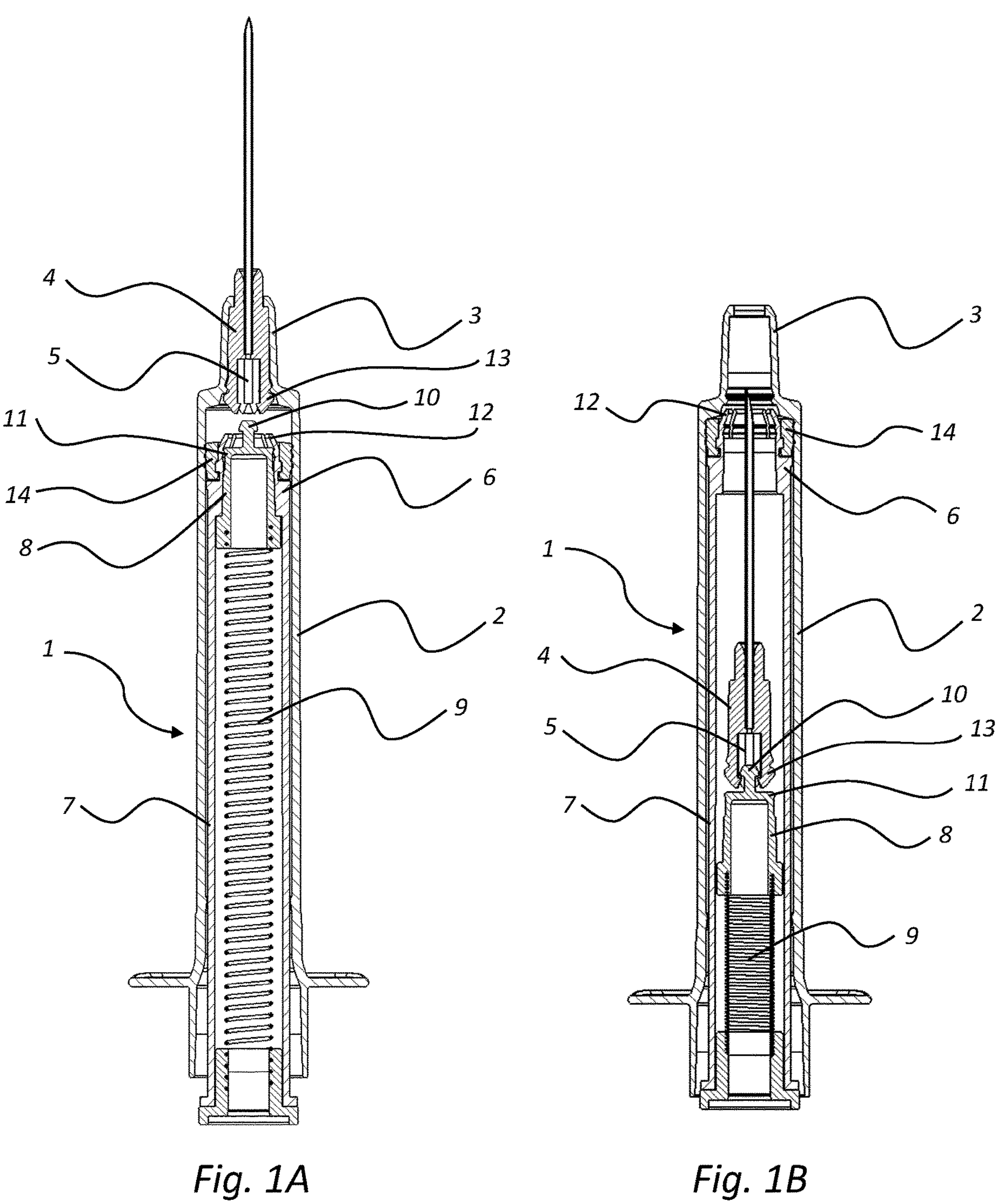
FIGS. 1A and 1B show an overall view of a syringe according to an embodiment of the present invention. The syringe depicted therein has an improved needle retraction mechanism, and comprises a cylindrical barrel 1, said barrel comprising a hollow body 2 and a hollow nose end 3. The syringe further comprises a needle holder 4 positioned in said nose end 3, said needle holder 4 comprising an internal cavity 5. A hollow plunger 6 is positioned within said hollow body 2 of said cylindrical barrel 1, which is connected to a rod 7, which rod extends into said hollow body 2 of said cylindrical barrel 1, and wherein each of said rod and said plunger has an axial hole passing therethrough. The syringe comprises an extractor element 8 which is positioned within said axial hole of said plunger 6 and within said hole of said rod 7, a recovery tension spring 9 positioned within said hole of said rod 7 and connected to said extractor element 8, said extractor element 8 being movably displaceable from an advanced position, surrounded by said plunger 6 with a portion protruding from said plunger 6 in the needle holder 4 direction, and a retracted position, fully retracted into said rod 7, positioned away from said needle holder 4, said extractor element 8 having a male protrusion 10, protruding from said plunger 6 in said advanced position to engage said internal cavity of said needle holder 5 to join said extractor 8 element to said needle holder 5, and hooking means 11 defining a connection between said plunger 6 and said extractor element 8 to maintain said extractor element 8 in said advanced position and to maintain the recovery spring 9 under tension. The axial hole of the plunger 6 is defined by a plurality of bendable flanges 12 which are configured to slide over the needle holder 5, said bendable flanges 12 thereby bending outwardly and expanding the axial hole of the plunger 6, and whereby the extractor element 8 is disconnected from said plunger 6 and is retracted towards its retracted position.
Figure 2A:
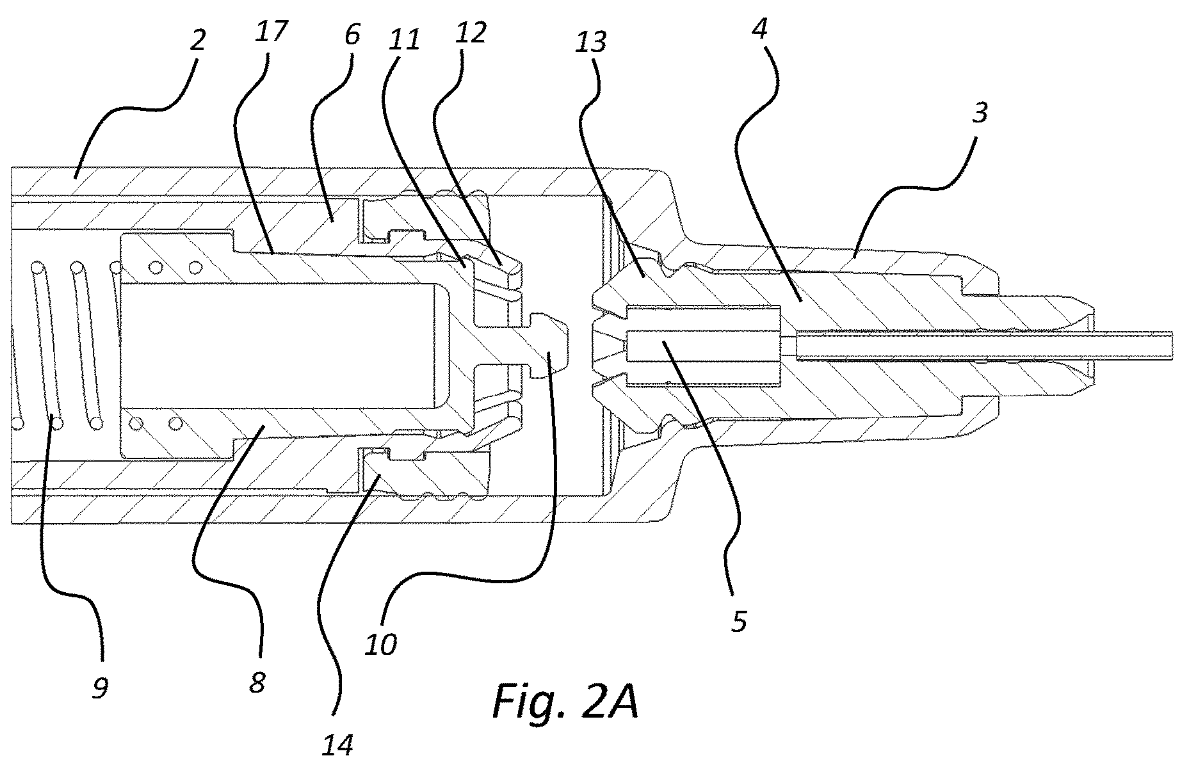
FIGS. 2A, 2B and 2C show a detailed view of a needle retraction mechanism of a syringe according to an embodiment of the present invention advancing through engagement of the retraction mechanism. In particular.
Figure 2B:
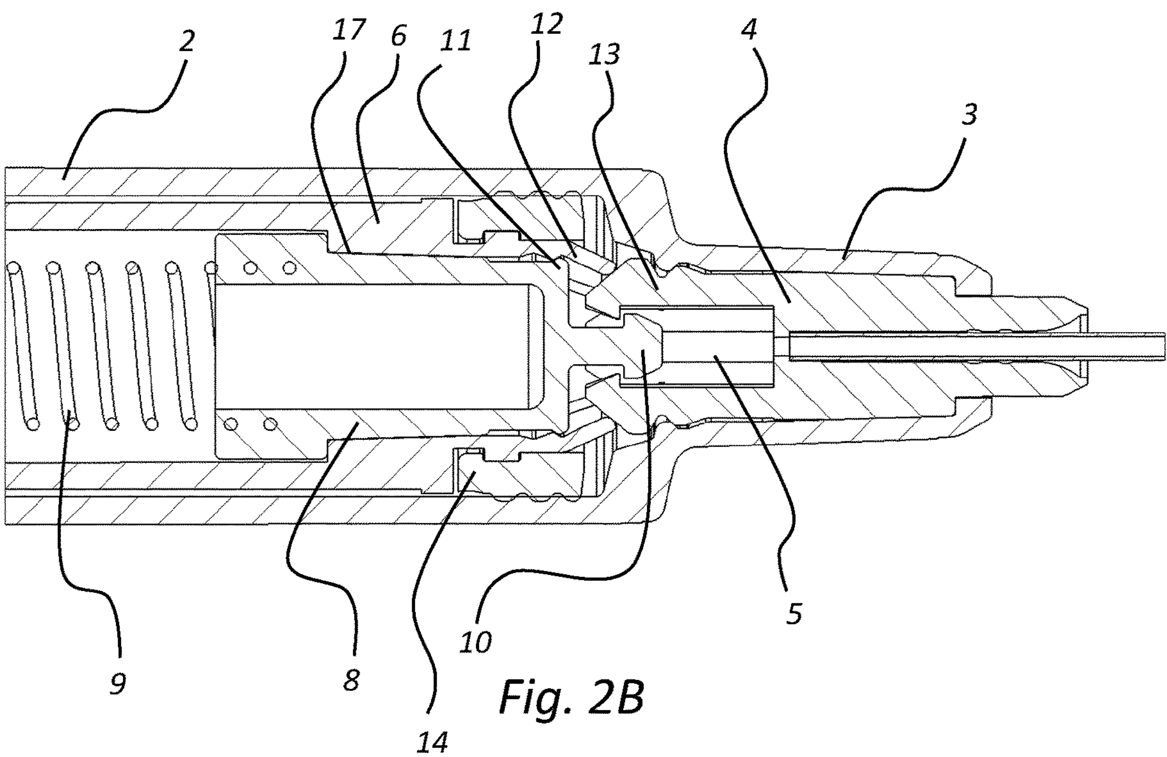
Figures 2C, 3:
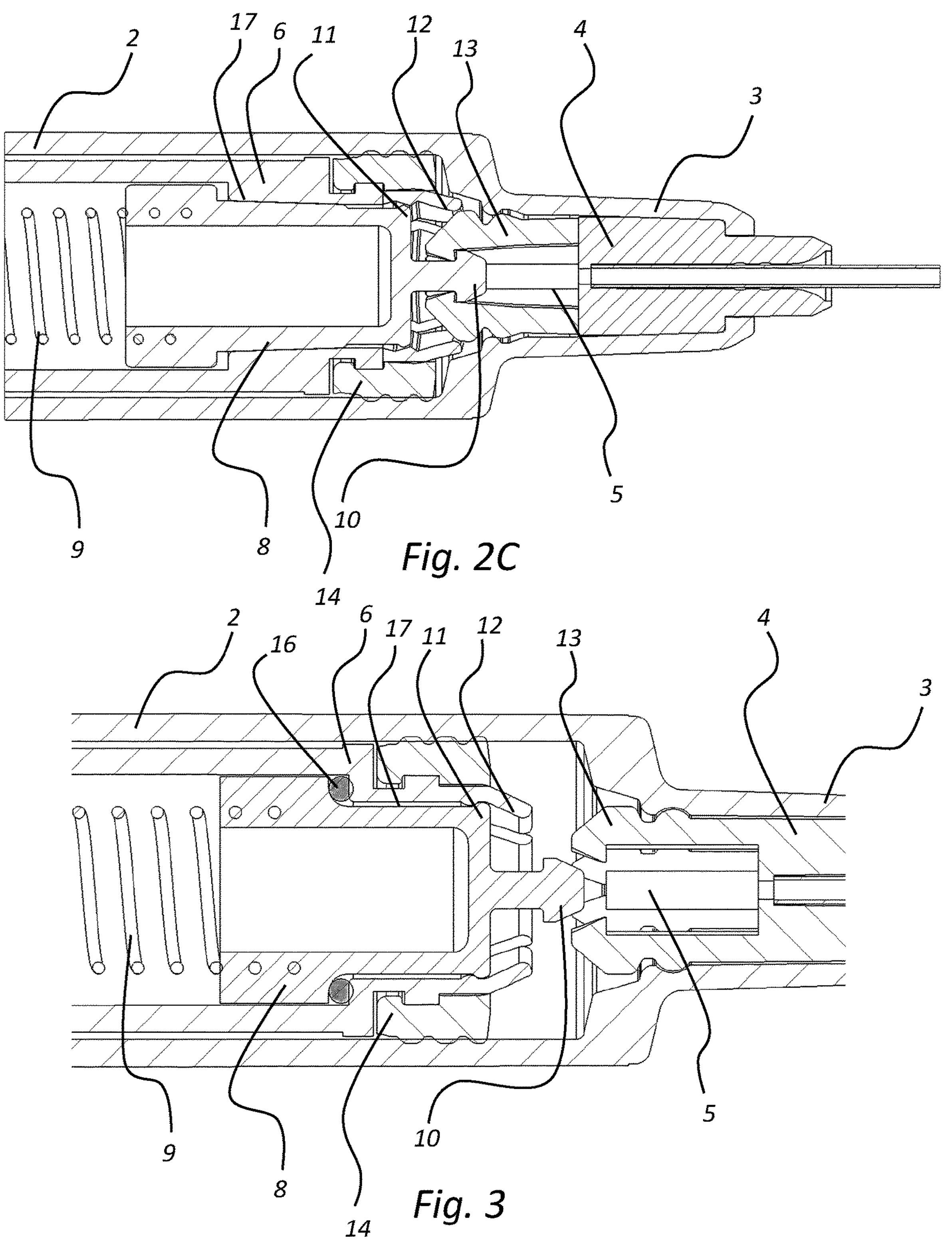
FIG. 3 shows a detailed view of a needle retraction mechanism, present in an empty syringe according to an embodiment of the present invention. The following is shown: the barrel 1 comprising the hollow body 2, the hollow nose end 3, the needle holder 4, the internal cavity 5 of the needle holder 4, the hollow plunger 6, the rod 7, the extractor element 8, the recovery tension spring 9, the male protrusion 10 of the extractor element 8, the hooking means 11 between the plunger 6 and the extractor element 8, and the bendable flanges 12 of the hollow plunger 6. Furthermore, the internal cavity 5 of the needle holder 4 is defined by a plurality of bendable grips 13, which are configured to slide over the male protrusion of the extractor element 8, said bendable grips 13 thereby bending outwardly, and whereby the male protrusion 10 of the extractor element 8 is inserted inside the internal cavity 5 of the needle holder 4. Connection of the extractor element 8 to the needle holder 4 is particularly smooth, for which operation of a (pre-filled) syringe kit according to the present invention does not feel markedly different to the operator compared to operating a regular syringe. Meanwhile, the provided bendable grips 13 allow a sturdy and irreversible coupling of the extractor element 8 to the needle holder 4. The plurality of bendable grips 13 are furthermore configured to slide inside the axial hole of the plunger 6, said bendable grips 13 thereby bending inwardly, and whereby the male protrusion 10 of the extractor element 8 is locked inside the internal cavity 5 of the needle holder 4. Upon engagement of the retraction mechanism, the described bending of the bendable grips 13 towards the inside of the syringe furthermore ensures a sturdy coupling of the extractor element 8 to the needle holder 4 including the needle 21. The bendable grips 13 depicted herein are particularly bendable over an angle of between −20° and 20° relative to the axial centerline of the syringe. The (pre-filled) syringe kit shown herein furthermore comprises a gasket 14, which gasket is fitted surrounding the plunger 6 at its needle holder 4 end, and wherein said gasket 14 is fitted between the outside of the plunger 6 and the inside of the hollow body 2 of the cylindrical barrel 1, and wherein the gasket 14 at least partially overlaps the plurality of bendable flanges 12. In the depicted embodiment, the hollow body 2 and the hollow nose end 3 of the cylindrical barrel 1 are provided as a single unit. The extractor element 8 is air-tightly configured inside the hollow plunger 6 by means of a conical fitting 17 between the inside wall of the plunger 6 and the outside wall of the extractor element 8.
Figure 4:
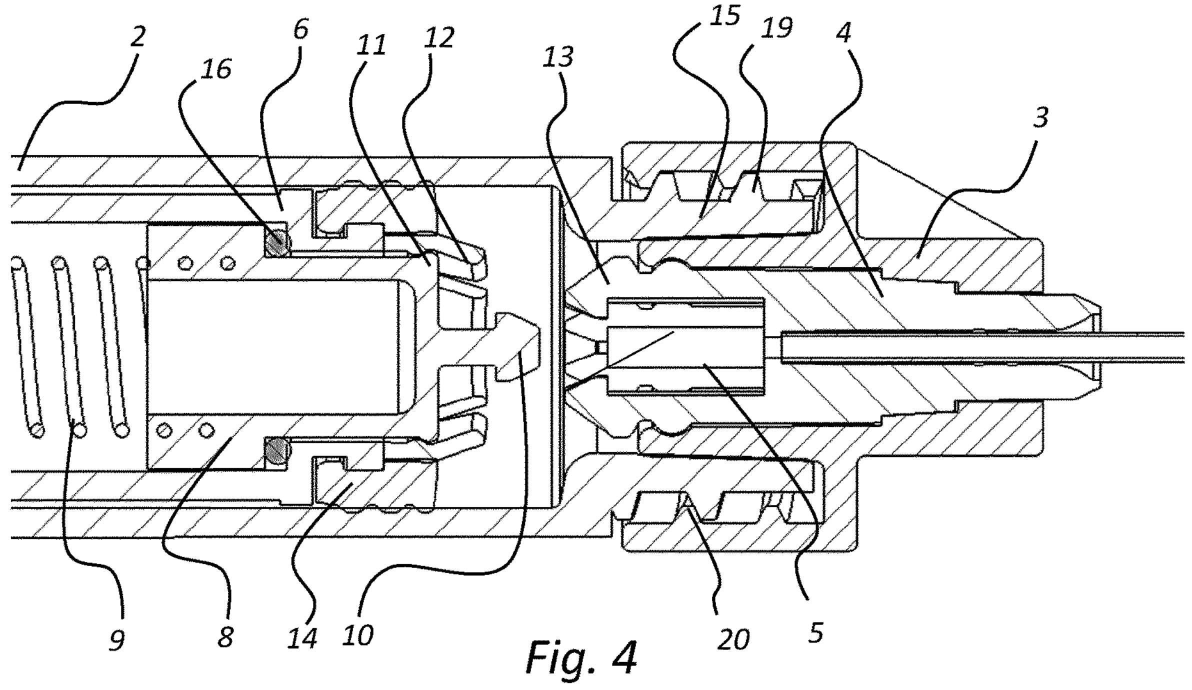
FIG. 4 shows a detailed view of a needle retraction mechanism of a syringe according to an embodiment of the present invention comprising a cylindrical or conical fitting 15 for an interchangeable needle holder. The hollow body 3 and the hollow nose end 2 of the cylindrical barrel are provided as two independent units, wherein the hollow body 2 extends in a fitting 15 comprising an axial hole. Said axial hole of the fitting 15 is accommodated to at least partly receive the hollow nose end 3, and which fitting 15 is furthermore configured with a first connective part 19 for connecting with a complementary second connective part 20 integral to the hollow nose end 3 and to permit the connection of said hollow nose end 3 to the hollow body 2 of the cylindrical barrel 1. These provisions allow the selection of a certain needle holder 4, in particular a certain needle 21, to be fitted in the hollow nose end 3 of the syringe.
Figures 5, 6:
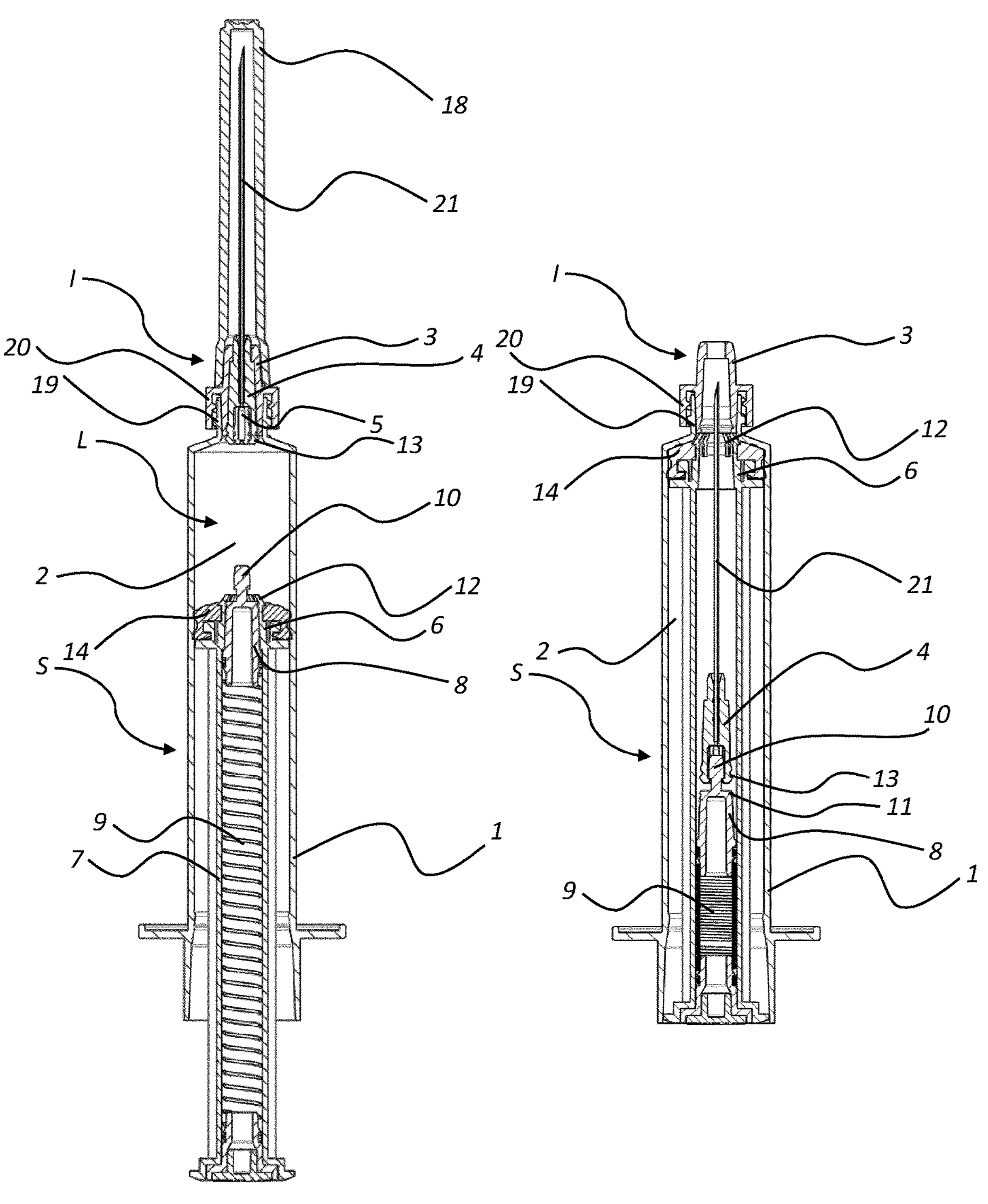
FIGS. 5 and 6 show an overall view of a (pre-filled) syringe kit according to an embodiment of the present invention. The syringe kit depicted therein has an improved needle retraction mechanism for ease and safety of use (as described in the foregoing Figures). The syringe kit comprises a syringe assembly S and an injection assembly I. The latter comprises a hollow nose end 3 and a needle holder 4 positioned therein. Said needle holder 4 comprises an internal cavity 5. The syringe assembly S comprises a barrel 1 with a hollow body 2, said hollow body 2 comprising an injectable liquid L, and further comprises a hollow plunger 6 positioned within said hollow body 2 of said cylindrical barrel 1, which is connected to a rod 7, which rod extends into said hollow body 2 of said cylindrical barrel 1, and wherein each of said rod and said plunger has an axial hole passing therethrough. The syringe assembly S comprises an extractor element 8 which is positioned within said axial hole of said plunger 6 and within said hole of said rod 7, a recovery tension spring 9 positioned within said hole of said rod 7 and connected to said extractor element 8, said extractor element 8 being movably displaceable from an advanced position, surrounded by said plunger 6 with a portion protruding from said plunger 6 in the needle holder 4 direction, and a retracted position, fully retracted into said rod 7, positioned away from said needle holder 4, said extractor element 8 having a male protrusion 10, protruding from said plunger 6 in said advanced position to engage said internal cavity of said needle holder 5 to join said extractor 8 element to said needle holder 5, and hooking means 11 defining a connection between said plunger 6 and said extractor element 8 to maintain said extractor element 8 in said advanced position and to maintain the recovery spring 9 under tension. The axial hole of the plunger 6 is defined by a plurality of bendable flanges 12 which are configured to slide over the needle holder 5, said bendable flanges 12 thereby bending outwardly and expanding the axial hole of the plunger 6, and whereby the extractor element 8 is disconnected from said plunger 6 and is retracted towards its retracted position.
Figure 7:
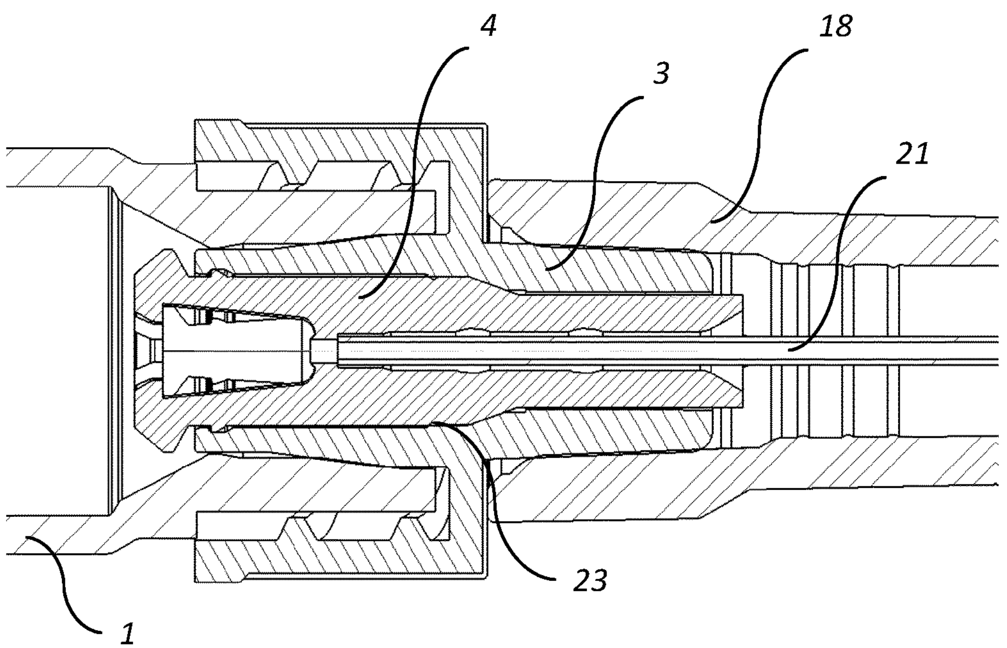

A specific embodiment according to the current invention is shown in FIG. 7, wherein the inside surface of the cylindrical barrel 3 is provided with an annular ring 23, which ring is configured to contact and support the outer perimeter of the needle holder 4.

Figure 8:
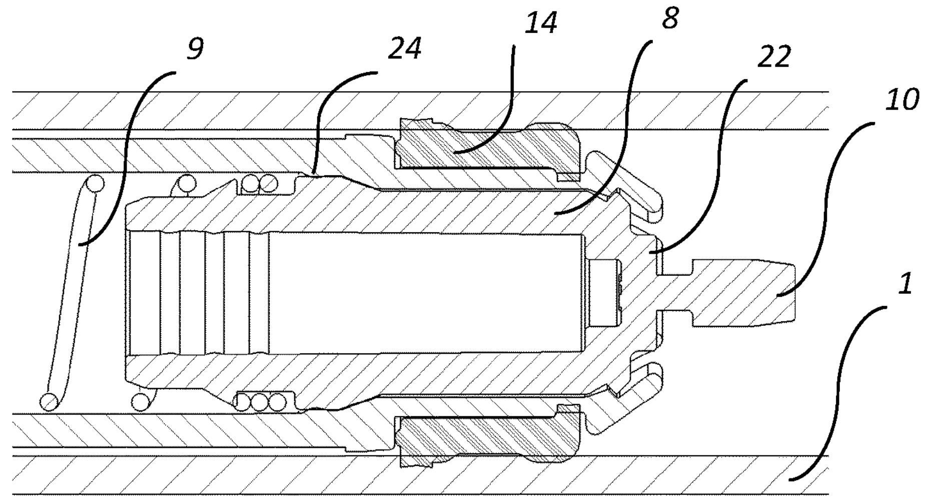

Yet another specific embodiment according to the current invention is shown in FIG. 8, wherein the extractor element 8 is provided with a dead space filler 22 extending from the distal end of the extractor element 8. The distal end of said dead space filler 22 providing a base from which the male protrusion of the of the extractor element 10 now protrudes. The inner surface of the hollow plunger 6 is shown in this figure provided with annular ring 24, which annular ring 24 is configured to provide a contact surface between the extractor element 8 and the inner surface of the hollow plunger 6.

Figure 9:
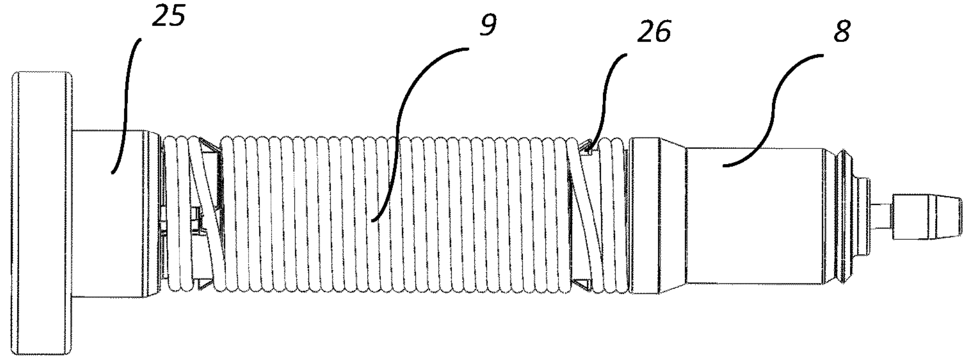

FIG. 9 illustrates a plunger cap 25 and an extractor element 8 attached to a recovery tension spring 9, which plunger cap 25 and which extractor element 8 are further equipped with a plurality of radially extending spring retention springs 26. In this figure, the proximal end of recovery tension spring 9 is shown with its first two coils surrounding the plunger cap 25 which two coils are retained by a plurality of spring retaining fins 26. Also in this figure, the distal end of the same recovery tension spring 9 is shown with its two last coils surrounding the proximal end of the extractor element 8, and which two coils are also retained by a plurality of spring retaining fins 26.

Figure 10:
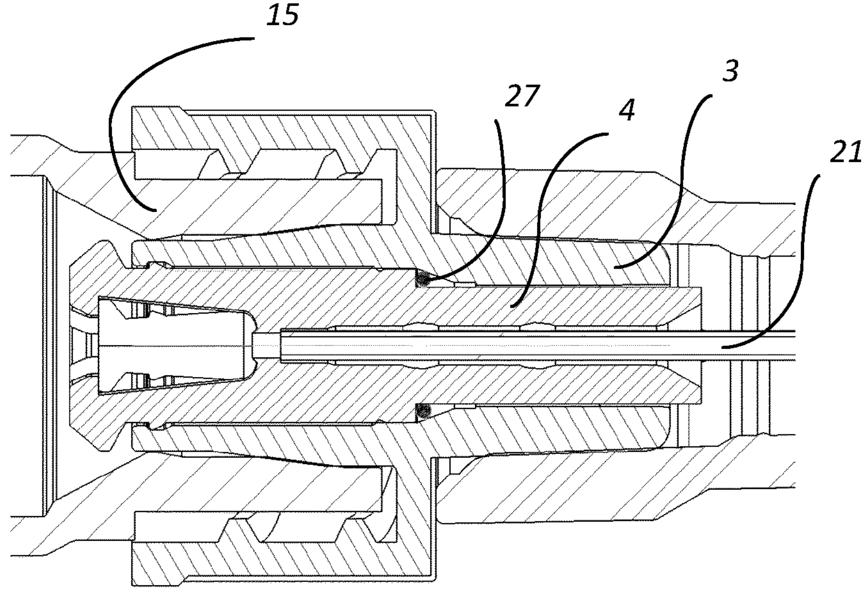

FIG. 10 illustrates yet another embodiment wherein a needle holder 4 of substantially cylindrical is shown in air-tight connections with a hollow nose end of the cylindrical barrel 3. Said air tight connection is provided by a gasket 27 provided between the perimeter of the needle holder 4 and a conical surface inside said hollow nose end of the cylindrical barrel 3.

LIST OF NUMBERED ITEMS

S syringe assembly
I injection assembly
L injectable liquid
1 cylindrical barrel
2 hollow body of the cylindrical barrel
3 hollow nose end of the cylindrical barrel
4 needle holder
5 internal cavity of the needle holder
6 hollow plunger
7 rod
8 extractor element
9 recovery tension spring
10 male protrusion of the extractor element
11 hooking means between the plunger and the extractor element
12 bendable flanges of the hollow plunger
13 bendable grips of the needle holder
14 gasket
15 fitting of the barrel
16 sealing ring
17 conical fitting
18 needle cap
19 first connective part
20 second connective part
21 needle
22 dead space filler
23 hollow nose annular ring
24 plunger annular ring
25 plunger cap
26 spring retention fin
27 needle holder gasket

The invention claimed is:

1. A syringe with an improved needle retraction mechanism, comprising:

a. a cylindrical barrel comprising a hollow body and a hollow nose end;

b. a needle holder positioned in said nose end, wherein said needle holder comprises an internal cavity;

c. a hollow plunger positioned within said hollow body of said cylindrical barrel;

d. a rod connected to or integral with said plunger and extending into said hollow body of said cylindrical barrel, wherein each of said rod and said plunger has an axial hole passing therethrough;

e. an extractor element is positioned within said axial hole of said plunger and within said hole of said rod;

f. a recovery tension or compression spring connected to said extractor element;

said extractor element being movably displaceable from an advanced position, surrounded by said plunger with a portion protruding in the needle holder direction, and a retracted position, fully retracted into said rod, positioned away from said hollow nose end;

said extractor element having a male protrusion, protruding in said advanced position to engage said internal cavity of said needle holder to join said extractor element to said needle holder, and hooking means defining a connection between said plunger and said extractor element to maintain said extractor element in said advanced position and to maintain the recovery spring under tension or compression;

characterized in that, the axial hole of the plunger is defined by at least two bendable flanges which are configured to slidably engage with the needle holder, said bendable flanges thereby bending outwardly and expanding the axial hole of the plunger, and whereby the extractor element is disconnected from said plunger and is retracted towards its retracted position.

2. The syringe according to claim 1, characterized in that, said at least two bendable flanges are bendable over an angle of between 0° and −45° relative to the axial centerline of the syringe.

3. The syringe according to claim 1, characterized in that the hooking means are complementary protrusions extending from both the hollow plunger and the retractor element.

4. The syringe according to claim 1, characterized in that, said internal cavity of the needle holder is defined by at least two bendable grips, which are configured to slide over the male protrusion of the extractor element, said bendable grips thereby bending outwardly, and whereby the male protrusion of the extractor element is inserted inside the internal cavity of the needle holder.

5. The syringe according to claim 4, wherein the plurality of bendable grips are configured to slide inside the axial hole of the plunger, said bendable grips thereby bending inwardly, and whereby the male protrusion of the extractor element is locked inside the internal cavity of the needle holder.

6. The syringe according to claim 4, characterized in that, said plurality of bendable grips are bendable over an angle of between −20° and 20° relative to the axial centerline of the syringe.

7. The syringe according to claim 1, characterized in that, the needle holder is air-tightly configured inside the hollow nose end, wherein the inside wall of the hollow nose end and the outside wall of the needle holder are complementary, conically shaped.

8. The syringe according to claim 1, wherein the syringe further comprises a gasket, which gasket is fitted surrounding the plunger at its needle holder end, and wherein said gasket is fitted between the outside of the plunger and the inside of the hollow body of the cylindrical barrel, characterized in that, the gasket at least partially overlaps the plurality of bendable flanges.

9. The syringe according to claim 1, characterized in that, the hollow body and the hollow nose end of the cylindrical barrel are provided as a single unit.

10. The syringe according to claim 1, characterized in that, the hollow body and the hollow nose end of the cylindrical barrel are provided as two independent units, wherein the hollow body extends in a fitting comprising an axial hole, which axial hole of the fitting is accommodated to at least partly receive the hollow nose end, and which fitting is furthermore configured with connecting means for connecting the hollow nose end to the hollow body of the cylindrical barrel.

11. The syringe according to claim 1, characterized in that, the extractor element is air-tightly configured inside the hollow plunger by means of a sealing ring fitted in between the inside wall of the plunger and the outside wall of the extractor element.

12. The syringe according to claim 1, characterized in that, the extractor element is air-tightly configured inside the hollow plunger, wherein the inside wall of the hollow plunger and the outside wall of the extractor element are complementary, conically shaped.

13. A syringe kit, said syringe kit comprising a syringe assembly and an injection assembly, said syringe assembly comprising:

a. a cylindrical barrel comprising a hollow body, wherein the hollow body is at least partly filled with an injectable liquid;

b. a hollow plunger positioned within said hollow body of said cylindrical barrel;

c. a rod connected to or integral with said plunger and extending at least partly into said hollow body of said cylindrical barrel, wherein each of said rod and said plunger has an axial hole passing therethrough;

d. an extractor element is positioned within said axial hole of said plunger and within said hole of said rod;

e. a recovery tension or compression spring connected to said extractor element; and said injection assembly comprising:

a. a hollow nose end; and b. a needle holder positioned in said nose end, wherein said needle holder comprises an internal cavity; wherein the syringe assembly and the injection assembly respectively comprise a first connective part and a second connective part, said first and second connective part are configured to allow both a closed kit configuration and an open kit configuration, said closed kit configuration comprising the air-tight connection of the syringe assembly to the injection assembly, wherein the internal cavity of the needle holder and the hollow body of the cylindrical barrel are configured to form a continuous channel which allows the passage of the injectable liquid, and said open kit configuration comprising the air-tight sealing of the syringe assembly without connection of the injection assembly;

the extractor element is movably displaceable from an advanced position, surrounded by said plunger with a portion protruding in the first connective part direction, and a retracted position, fully retracted into said rod, positioned away from said first connective part;

the extractor element has a male protrusion, protruding in said advanced position to engage said internal cavity of said needle holder to join said extractor element to said needle holder, and hooking means defining a connection between said plunger and said extractor element to maintain said extractor element in said advanced position and to maintain the recovery spring under tension or compression;

characterized in that, the axial hole of the plunger is defined by a at least two bendable flanges which are configured to slidably engage with the needle holder, said bendable flanges thereby bending outwardly and expanding the axial hole of the plunger, and whereby the extractor element is disconnected from said plunger and is retracted towards its retracted position.

14. The syringe kit according to claim 13, wherein the first connective part and the second connective part of the respective syringe assembly and the injection assembly are air-tightly connected to each other.

15. The syringe kit according to claim 13, wherein the first connective part and the second connective part of the respective syringe assembly and the injection assembly are disconnected from each other, and wherein the hollow body of the barrel is air-tightly sealed by means of a closure cap fitted to the first connective part of the syringe assembly.

16. The syringe kit according to claim 13, characterized in that, said plurality of bendable flanges are bendable over an angle of between 0° and −45° relative to the axial centerline of the syringe.

17. The syringe kit according to claim 13, characterized in that the hooking means are complementary protrusions extending from both the hollow plunger and the retractor element.

18. The syringe kit according to claim 13, characterized in that, said internal cavity of the needle holder is defined by at least two bendable grips, which are configured to slide over the male protrusion of the extractor element, said bendable grips thereby bending outwardly, and whereby the male protrusion of the extractor element is inserted inside the internal cavity of the needle holder.

19. The syringe kit according to claim 18, wherein the plurality of bendable grips are configured to slide inside the axial hole of the plunger, said bendable grips thereby bending inwardly, and whereby the male protrusion of the extractor element is locked inside the internal cavity of the needle holder.

20. The syringe kit according to claim 18, characterized in that, said plurality of bendable grips are bendable over an angle of between −20° and 20° relative to the axial centerline of the syringe.

21. The syringe kit according to claim 13, characterized in that, the needle holder is air-tightly configured inside the hollow nose end, wherein the inside wall of the hollow nose end and the outside wall of the needle holder are complementary, conically shaped.

22. The syringe kit according to claim 13, wherein the syringe further comprises a gasket, which gasket is fitted surrounding the plunger at its needle holder end, and wherein said gasket is fitted between the outside of the plunger and the inside of the hollow body of the cylindrical barrel, characterized in that, the gasket at least partially overlaps the plurality of bendable flanges.

23. The syringe kit according to claim 13, characterized in that, the extractor element is air-tightly configured inside the hollow plunger by means of a sealing ring fitted in between the inside wall of the plunger and the outside wall of the extractor element.

24. The syringe kit according to claim 13, characterized in that, the extractor element is air-tightly configured inside the hollow plunger, wherein the inside wall of the hollow plunger and the outside wall of the extractor element are complementary, conically shaped.

25. Use of the syringe kit according to claim 13 for the injection of the injectable liquid in a subject, wherein the syringe assembly and the injection assembly are connected to each other prior to injection.

26. A method of manufacturing a syringe kit, comprising:

assembling or providing a syringe assembly comprising the following parts:

a. a cylindrical barrel comprising a hollow body;

b. a hollow plunger positioned within said hollow body of said cylindrical barrel;

c. a rod connected to or integral with said plunger and extending at least partly into said hollow body of said cylindrical barrel, wherein each of said rod and said plunger has an axial hole passing therethrough;

d. an extractor element is positioned within said axial hole of said plunger and within said hole of said rod; and e. a recovery tension or compression spring connected to said extractor element;

assembling or providing a needle assembly comprising the following parts:

a. a hollow nose end; and b. a needle holder positioned in said nose end, wherein said needle holder comprises an internal cavity; wherein the syringe assembly and the injection assembly respectively comprise a first connective part and a second connective part, said first connective part allowing the air-tight sealing of the hollow body of the barrel, and the air-tight connection to the second connective part of the injection assembly, wherein the internal cavity of the needle holder and the hollow body of the cylindrical barrel are configured to form a continuous channel which allows the passage of the injectable liquid, the extractor element is movably displaceable from an advanced position, surrounded by said plunger with a portion protruding in the first connective part direction, and a retracted position, fully retracted into said rod, positioned away from said first connective part;

the extractor element has a male protrusion, protruding in said advanced position to engage said internal cavity of said needle holder to join said extractor element to said needle holder, and hooking means defining a connection between said plunger and said extractor element to maintain said extractor element in said advanced position and to maintain the recovery spring under tension or compression; and wherein the axial hole of the plunger is defined by at least two bendable flanges which are configured to slidably engage with the needle holder, said bendable flanges thereby bending outwardly and expanding the axial hole of the plunger, and whereby the extractor element is disconnected from said plunger and is retracted towards its retracted position;

filling the hollow body of the cylindrical barrel at least partly with an injectable liquid;

air-tightly closing the hollow body of the cylindrical barrel.

27. The method according to claim 26, wherein the hollow body is at least partly filled with the injectable liquid, and wherein said first and second connective part are configured to allow both a closed kit configuration and an open kit configuration, said closed kit configuration comprising the air-tight connection of the syringe assembly to the injection assembly, and said open kit configuration comprising the air-tight sealing of the syringe assembly without connection of the injection assembly.

* * * * *